(12) United States Patent
Fischer

(10) Patent No.: US 9,308,014 B2
(45) Date of Patent: Apr. 12, 2016

(54) MULTIFUNCTION DEVICE FOR ENDOSCOPIC SURGERY

(75) Inventor: Klaus Fischer, Nagold (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1999 days.

(21) Appl. No.: 12/296,853

(22) PCT Filed: Apr. 3, 2007

(86) PCT No.: PCT/EP2007/003001
§ 371 (c)(1),
(2), (4) Date: Oct. 10, 2008

(87) PCT Pub. No.: WO2007/118608
PCT Pub. Date: Oct. 25, 2007

(65) Prior Publication Data
US 2009/0125027 A1    May 14, 2009

(30) Foreign Application Priority Data

Apr. 11, 2006 (DE) .......................... 10 2006 017 014
Jun. 16, 2006 (DE) .......................... 10 2006 027 873

(51) Int. Cl.
*A61B 18/14* (2006.01)
*A61B 17/3203* (2006.01)
*A61B 17/32* (2006.01)
*A61B 18/12* (2006.01)

(52) U.S. Cl.
CPC ......... *A61B 17/3203* (2013.01); *A61B 18/1445* (2013.01); *A61B 17/32* (2013.01); *A61B 2018/1253* (2013.01); *A61B 2018/142* (2013.01)

(58) Field of Classification Search
CPC ........... A61B 17/3203; A61B 18/1445; A61B 18/085; A61B 2018/1253; A61B 2018/142; A61B 2018/1472
See application file for complete search history.

(56) References Cited

U.S. PATENT DOCUMENTS

| | | | |
|---|---|---|---|
| 4,898,574 A * | 2/1990 | Uchiyama et al. | 604/22 |
| 5,169,397 A * | 12/1992 | Sakashita et al. | 606/27 |
| 5,474,571 A * | 12/1995 | Lang | 606/205 |
| 5,527,330 A | 6/1996 | Tovey | |
| 5,766,169 A * | 6/1998 | Fritzsch et al. | 606/48 |
| 5,921,916 A * | 7/1999 | Aeikens et al. | 600/108 |

(Continued)

FOREIGN PATENT DOCUMENTS

DE    37 15 418 A1    11/1987
DE    44 20 608 A1    12/1995

(Continued)

OTHER PUBLICATIONS

European Search Report, Nov. 13, 2009.

*Primary Examiner* — Nathan R Price
*Assistant Examiner* — Justin L Zamory
(74) *Attorney, Agent, or Firm* — Blank Rome LLP

(57) ABSTRACT

A multifunction device for endoscopic surgery including a supply means for the supply of at least one fluid and forceps or a clamp which comprise forceps-shaped electrodes with jaw parts for high-frequency surgery. The supply means is formed to dissect tissue by means of a fluid jet at or in a jaw part of the forceps or clamp. The multifunction device is one for both water jet surgery and high-frequency coagulation and/or cutting that occupies no more space than a conventional high-frequency instrument or conventional forceps or clamps.

12 Claims, 3 Drawing Sheets

(56) References Cited

U.S. PATENT DOCUMENTS

| | | | |
|---|---|---|---|
| 6,091,451 A * | 7/2000 | Farr et al. | 348/342 |
| 2004/0186348 A1 | 9/2004 | Kidooka | |
| 2004/0199226 A1 * | 10/2004 | Shadduck | 607/96 |

FOREIGN PATENT DOCUMENTS

| | | |
|---|---|---|
| DE | 296 10 479 U1 | 10/1996 |
| DE | 42 42 143 C2 | 4/2001 |
| DE | 100 56 238 A1 | 5/2002 |
| DE | 10 2004 013419 A1 | 9/2004 |
| DE | 10 2004 020855 A1 | 11/2005 |
| EP | 0 280 972 A | 9/1988 |
| EP | 1 607 771 A1 | 12/2005 |
| EP | 1 720 050 A1 | 11/2006 |
| JP | 2003-220064 A2 | 8/2003 |
| JP | 2004-275548 A2 | 10/2004 |

* cited by examiner

MULTIFUNCTION DEVICE FOR ENDOSCOPIC SURGERY

FIELD OF THE INVENTION

The invention relates to a multifunction device for endoscopic surgery, in particular an instrument which combines water jet surgery and high-frequency surgical applications in a single device.

BACKGROUND OF THE INVENTION

Minimally invasive surgery is a generic term for operative interventions with minimal trauma. It has always been the objective of operative treatment to bring about rapid recovery with minimal discomfort after the operation. At the start of the 1990s, laparoscopic and endoscopic surgery initially established themselves only as simple operative interventions, but later also established themselves for carrying out complex operations.

Nowadays, a differentiation is made between laparoscopic surgery and endoscopy. In laparoscopic surgery, the same interventions are, for all intents and purposes, made as with open surgical methods. However, the largest difference as compared to conventional interventions is that the area to be operated on is reached by significantly smaller incisions than with the conventional open surgery methods.

In contrast, in endoscopy, a doctor can gain a good view into the natural body cavities and hollow organs of the patient, identify illnesses and possibly also treat them immediately without large-scale surgical intervention. To this end, flexible or rigid endoscopes are used to examine the organs and e.g. look at their mucous membrane. For this purpose, there are also endoscopes with different outer diameters, lengths, biopsy channel diameters and functions. Moreover, so-called interventional endoscopy is no longer used exclusively in diagnosis, but is also frequently used in the treatment of a wide range of illnesses.

Typical applications for laparoscopic surgery and/or interventional endoscopy are, for example, a selective tissue separation by high-frequency (HF) or water jet surgery and haemostasis (coagulation) or vascular sealing by HF forceps or electrodes. Furthermore, surgical forceps are also used for dissection or biopsy removal of tissue, or also only for tissue preparation or fixing.

Endoscopic mucosal resection (EMR), in which tumors with large surface areas in the gastrointestinal tract are removed, is carried out for example, with the help of water jet technology, whereby HF surgery is used for haemostasis (coagulation). In this case, the blood vessels, which were previously separated selectively from the tissue with water jet technology, are securely sealed in a targeted manner with HF forceps.

In water jet surgery, an extremely fine laminary water jet is used which, as it were, pushes apart the tissue and forms an expansion space. Soft tissue can, in principle, be dissected at a low pressure, whereby tissue with high elasticity or large expansion, such as for example, blood vessels, escape the water jet and are thus protected.

In contrast, in HF surgery, electrical energy is converted into heat and is thus able to separate biological tissue and also bring about haemostasis. Therein, it is mainly thermal effects which are utilized. Temperatures of 60° C. to 70° C. in the region around the HF surgery electrode lead to protein coagulation. The term coagulation is used to refer to this process. This "welding effect" can be used, for example, to stop bleeding.

During separation, as a result of a higher current density, temperatures of over 100° C. are achieved such that the fluid evaporates in an explosive manner, the space is enlarged and the cell membrane "bursts." Further, cells located in the direction of electrode movement follow this effect, as a result of which the desired incision or separation of the tissue is achieved.

In HF surgery, a differentiation is also made between monopolar and bipolar application technology. In the case of monopolar application technology, the flow of current takes place from a HF surgery electrode, through the biological tissue and to a neutral electrode, which is usually positioned on a large surface area on the patient. In contrast to this, in the case of bipolar application technology, the HF current does not flow across the body of the patient to a neutral electrode. In the case of bipolar forceps or clamps, an active electrode and a neutral electrode are arranged directly opposite one another, whereby the HF current only flows from the active electrode to the neutral electrode. This results in very short current paths and defined coagulation regions with a low power requirement.

During an operation (e.g., EMR) various instruments are frequently required for gripping, rinsing, separating and/or coagulating tissue and have to be interchanged correspondingly in the working channels. However, the continuous interchange of instruments requires a lot of time and can significantly extend the length of an operation.

A multifunction device, which comprises for example, an HF manual instrument for bipolar coagulation, cutting and gripping as well as a rinsing tube and suction tube additionally accommodated in a protective tube, is known from DE 42 42 143 C2. The tubes (rinsing, suction) which are accommodated in a protective tube, however, do not enable any selective separation of HF and water jet surgery and require, among other things, additional space since they are attached parallel to the electrodes on the manual instrument.

Furthermore, DE 100 56 238 A1 describes a device with a jaw mechanism for tube shaft instruments for the removal of intracorporal tissue samples which can be sucked away through a tube shaft in the proximal direction. The open jaw passage can additionally be used for rinsing or sucking away or also for the introduction of coagulation electrodes, lenses or other operational probes. However, the instruments and probes used must be correspondingly interchanged during the intervention.

It is therefore desirable to have available a multifunction device for endoscopic surgery which can be universally used and takes up little space.

SUMMARY

Embodiments of the invention include a multifunction device for endoscopic surgery with a supply means for the supply of at least one fluid and forceps or a clamp which comprise forceps-shaped electrodes with jaw parts for HF surgery, whereby the supply means is formed to dissect tissue by means of a fluid jet at or in a jaw part.

Embodiments of the invention also include a device for water jet surgery and HF electrodes formed for coagulation and/or for cutting in or at forceps or a clamp such that the multifunction device for surgery occupies no more space than a conventional HF instrument or conventional forceps or clamps.

As a result, a multifunction device for surgery is provided which combines the advantages of water jet surgery, in particular dissection by means of a fluid jet, with the advantages of HF surgery, in particular HF cutting and thermal coagulation, in forceps or a clamp and which is not larger than a conventional HF instrument.

One advantage of the multifunction device according to embodiments of the invention thus lies in particular in that, with the help of a single multifunction device for surgery, the functions of selective cutting, gripping and thermal coagulation of tissue can be carried out without the need to change instruments during the intervention. As a result, operating times, costs and the risk for the patient in terms of the length of intervention can be minimized.

According to a first embodiment, the endoscopic multifunction device for surgery includes forceps-shaped electrodes with a rigid part and a movable jaw part, whereby the supply means is formed for dissection by means of a fluid jet at or in the rigid jaw part. Herein, the rigid jaw part offers a simple possibility for integrating the supply means in one of the jaw parts and controlling it in accordance with the application.

The jaw part containing the supply means further includes an end piece which protrudes out of the distal end of the jaw part, whereby the end piece of the supply means is formed as a monopolar electrode which is suitable for the dissection and/or coagulation of tissue. The end piece of the supply means not only acts as a monopolar HF electrode for dissection of tissue but also acts as an outlet nozzle for precise cutting by water jet surgery.

The monopolar electrode preferably includes a circularly formed disc and/or a hemispherical attachment located at the distal end of the end piece of the supply means. This attachment simplifies HF cutting in all directions.

The end piece is furthermore movable relative to a longitudinal axis of the rigid jaw part. As a result, it is achieved that the length of the electrode can be adapted according to the desired use.

In another disclosed embodiment, at least one outlet of the supply means is arranged at the inside of the rigid jaw part opposite the movable jaw part such that at least one fluid jet can be discharged in the direction of the movable jaw part. As a result, it is achieved that precise tissue separation can be brought about in a simple manner, which is advantageous for example, in the case of partial liver resection. The tissue can be held in place by the jaw parts at the same time as resection. Furthermore, the jaw part opposite the outlet of the supply means offers, among other things, protection against the at least one fluid jet, which is discharged with very high pressure.

In a further disclosed embodiment, the at least one outlet of the supply means may be displaceable relative to a longitudinal axis of the rigid jaw part. As a result, it is achieved that the fluid jet can be displaced relative to the tissue fixed by the two jaw parts and the tissue separation is thus facilitated.

Furthermore, the at least one outlet of the supply means may be located in a recess of the rigid jaw part arranged parallel to a longitudinal axis of the multifunction device for surgery and/or the movable jaw part comprises a recess arranged parallel to the longitudinal axis of the multifunction device for surgery, which recess is opposite the at least one outlet of the supply means. As a result, it is achieved that the at least one outlet is kept free during separation by the fluid jet and additional fixing of the tissue to be separated and the exiting fluid can be discharged via the recesses.

in a further disclosed embodiment, the forceps or clamp is formed as biopsy forceps such that the multifunction device for surgery can be used for biopsy removal.

It is furthermore possible that the jaw parts of the multifunction device for surgery are prestressed by a spring element and as a result are held open. As a result, the function of gripping and coagulation is facilitated since the jaw parts only have to be actively closed but open again automatically as a result of the spring element.

BRIEF DESCRIPTION OF THE DRAWINGS

In the following, the invention will now be described in more detail with reference to an exemplary embodiment, which will be explained in more detail with reference to the enclosed drawings.

DETAILED DESCRIPTION OF THE INVENTION

The same reference numbers are used in the following description for identical parts and parts with identical effects.

Figure 1:
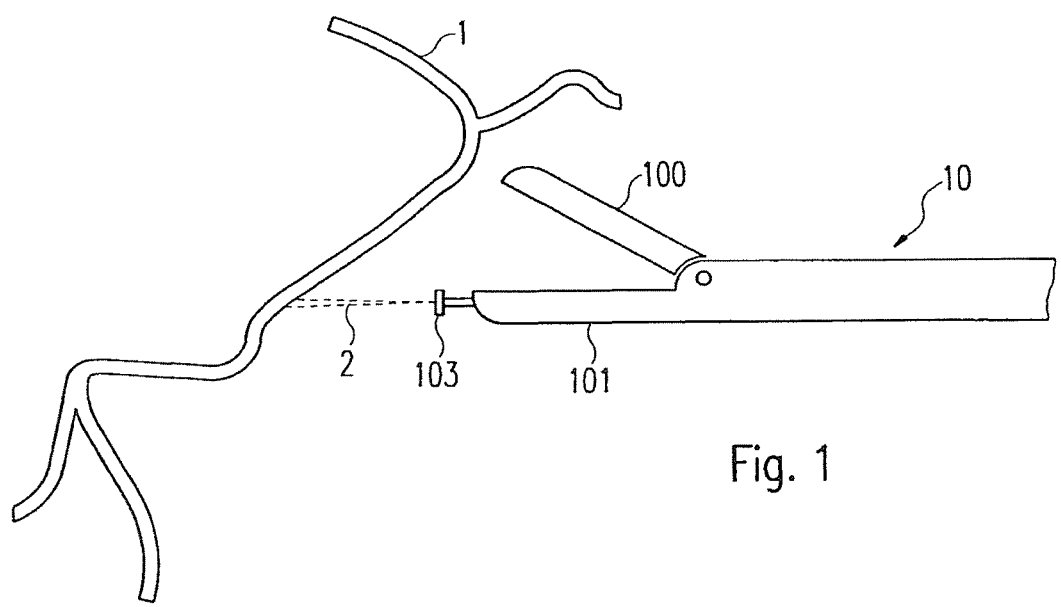
FIG. 1 illustrates a simplified view of a typical use of an embodiment of a multifunction device for surgery, wherein a blood vessel is freely prepared by the fluid jet and can subsequently be separated and coagulated.
Figure 2:
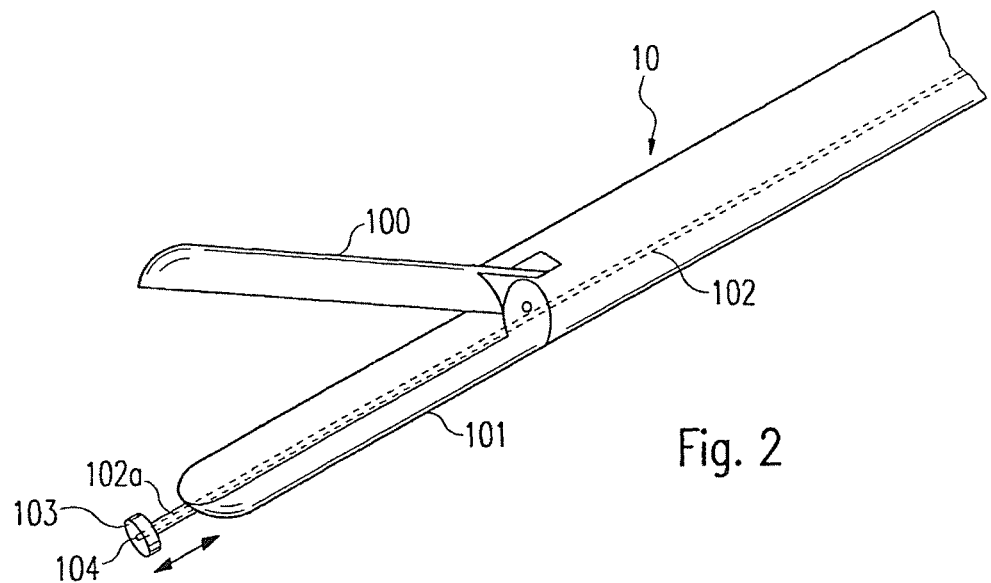
FIG. 2 illustrates a perspective view of an embodiment of a multifunction device for surgery according to the invention.

In the exemplary embodiment shown in FIGS. 1 and 2, a multifunction device for surgery 10 with forceps or a clamp with, in each case, a movable jaw part 100 and a rigid jaw part 101 is shown. Jaw parts 100, 101 are also formed as bipolar electrodes. A circular disc-shaped monopolar electrode 103 is attached to an end piece 102a of a supply means 102 integrated within rigid jaw part 101 and for formation of a fluid jet 2 of a fluid (e.g., NaCl solution). The multifunction device for surgery is formed in this case such that it can selectively dissect for example, tissue around a blood vessel 1 without damaging the blood vessel 1. After free preparation, blood vessel 1 is separated with bipolar electrodes 100, 101 of the forceps or clamp and "welded" by coagulation. Jaw parts 100, 101 formed as electrodes are in this case used for tissue separation as a result of a higher current flow between bipolar electrodes 100, 101 and the resultant higher temperatures. In addition, jaw parts 100, 101 formed as forceps or a clamp enable gripping or holding and thus enable preparation of the tissue, organ or blood vessel to be operated on. All the functions cited above are available with the multifunction device for surgery according to the invention without requiring a change in instrument. This can significantly reduce operating times and as a result minimize risks for the patient. Moreover, the forceps or clamp can be electrically isolated towards the outside in a further advantageous configuration.

Moreover, the means for supplying a fluid 102 with a correspondingly lower pressure of the fluid jet can also be used for injection or rinsing. Depending on the application, HF electrode 103 can be formed as a needle, hook, spatula, hemisphere, disc or in any other advantageous form. Moreover, HF-electrode 103 can be integrated into rigid jaw part 101 such that it is movable relative to a longitudinal axis of the rigid jaw part. Multifunction device for surgery 10 can furthermore be formed as a rigid or flexible instrument.

Figure 3:
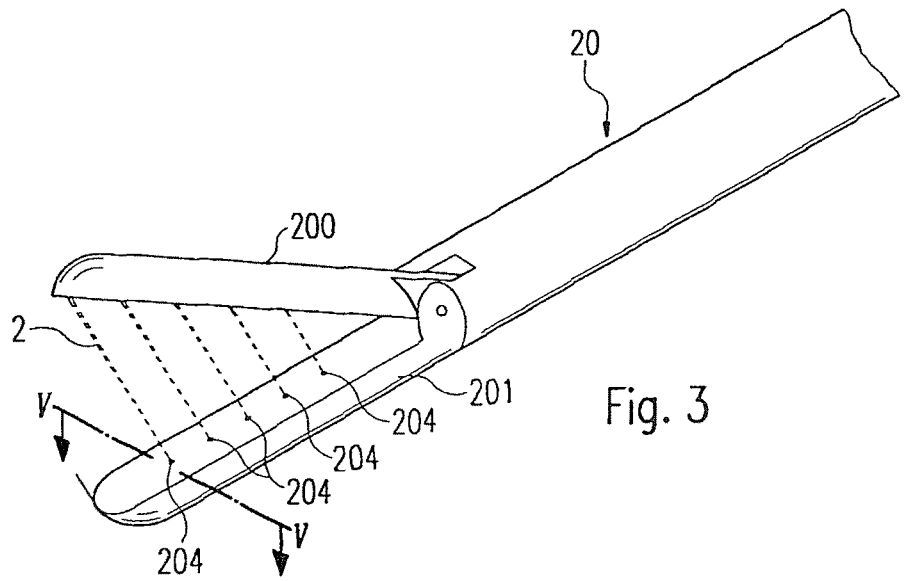
FIG. 3 illustrates a perspective view of a further embodiment of a multifunction device for surgery according to the invention with a fixed supply means.
Figure 4:
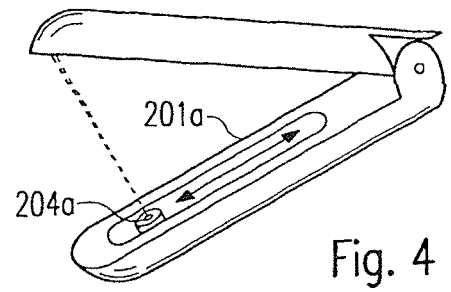
FIG. 4 illustrates a perspective view of a further embodiment of a multifunction device for surgery according to the invention with a movable supply means.
Figure 5:
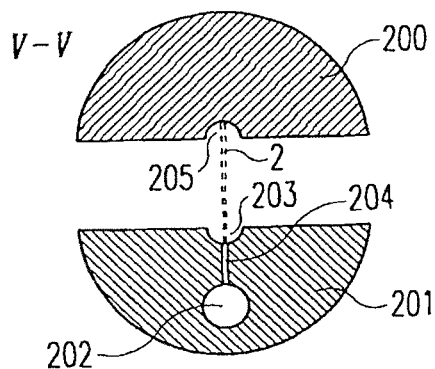
FIG. 5 illustrates a sectional view along line V-V in FIG. 3.

A further exemplary embodiment of the invention is shown in FIGS. 3, 4 and 5. This exemplary embodiment is particularly suitable for precise separation of tissue such as for example, in the case of partial liver resections. At least one outlet 204 of a supply means 202 for a fluid is arranged on an inside of rigid jaw part 201 which is opposite movable jaw part 200 such that at least one fluid jet 2 can be discharged in the direction of movable jaw part 200 with suitable pressure. In use, the open multifunction device for surgery 20 is moved with a sliding movement in the direction of the tissue and the tissue is separated by the at least one fluid jet. Outlets 204 are arranged in a recess 203 of rigid jaw part 201 in order to prevent blocking by the tissue. Movable jaw part 200 can also act as protection for tissue in the immediate vicinity against fluid jets 2 which are discharged with high pressure and thereby prevent a perforation of in-situ tissue parts. The fluid jet impacting on the movable jaw part is drained off by recess 205 (FIG. 5). FIG. 4 shows an embodiment with an outlet 204a which is displaceable relative to a longitudinal axis of rigid jaw part 102a.

Figure 6:
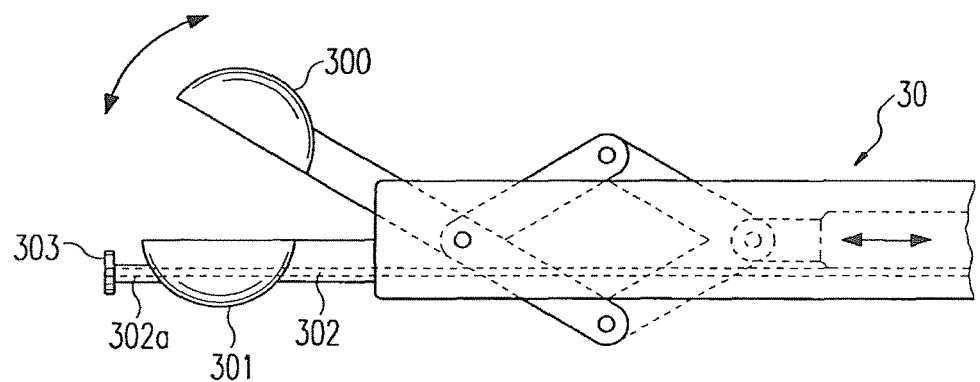
FIG. 6 illustrates a side view of a further embodiment of a multifunction device for surgery according to the invention which is formed as biopsy forceps.

The exemplary embodiment shown in FIG. 6 shows a multifunction device for surgery 30 with biopsy forceps specially formed for biopsy and which includes a rigid jaw part 301 and a movable jaw part 300. A supply means 302 for a fluid jet of a fluid (e.g., NaCl solution) is integrated in rigid jaw part 301. End piece 302a of supply means 302 protrudes out of rigid jaw part 302, whereby a circular disc-shaped monopolar electrode 303 is formed at the end of end piece 302a. The monopolar electrode at the end of end piece 302a may also have any other shape which is advantageous for HF cutting. The function of the gripping mechanism, which is known per se, of the biopsy forceps is, in this case, marked by arrows. The hidden parts of the gripping mechanism are shown by dashed lines. The exemplary embodiment according to the invention shown in FIG. 6 has the advantage that tissue parts can be selectively separated by HF or water jet surgery and thereafter immediately received with jaw parts 300, 301 of biopsy forceps 30 and transported away. In the case of low current strengths, monopolar electrode 303 could also be used for coagulation.

Figure 7:
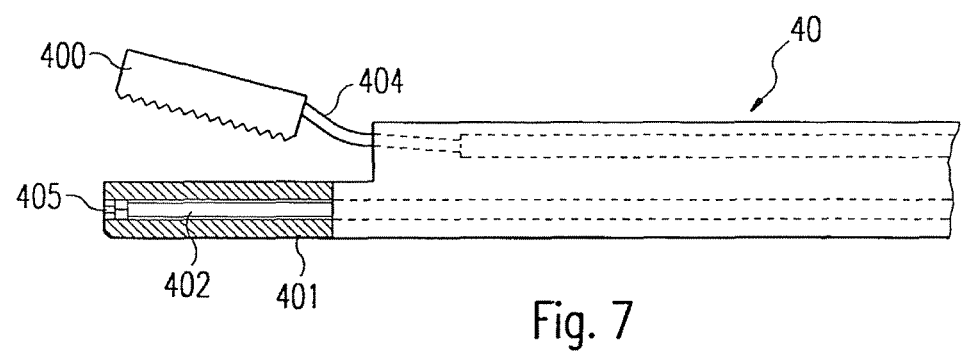
FIG. 7 illustrates a side view of a further embodiment of a multifunction device for surgery according to the invention, whereby the rigid jaw part is represented as a functional section.

A further exemplary embodiment of the invention is shown in FIG. 7. Movable jaw part 400 is prestressed by a spring element 404 such that it is held open. Furthermore, FIG. 7 shows a section through a rigid jaw part, whereby a supply means 402 and a nozzle 405 formed at the end of supply means 402 are integrated into the rigid jaw part 401 for forming a fluid jet. Rigid and movable jaw parts, 401, 400 are formed as bipolar electrodes for the coagulation of tissue and can also be used as HF cutting electrodes in the case of a corresponding current strength.

It should be pointed out here that all the above described parts and in particular the details illustrated in the drawings are essential for the invention alone and in combination. Adaptations thereof are the common practice of persons skilled in the art.

The invention claimed is:

1. A multifunction device for endoscopic surgery comprising:
a supply means for the supply of at least one fluid; and
forceps which comprises forceps-shaped electrodes with jaw parts for high-frequency surgery,
wherein the supply means is formed to dissect tissue by means of a fluid jet and is formed at or in one of the jaw parts,
wherein the forceps-shaped electrodes comprises a rigid jaw part and a movable jaw part and the supply means is formed at or within the rigid jaw part,
wherein an end piece of the supply means is a high-frequency electrode and protrudes out of a distal end of the rigid jaw part, and
wherein the end piece of the supply means is movable relative to a longitudinal axis of the rigid jaw part such that a length of the electrode can be adapted according to a use thereof.

2. A multifunction device for endoscopic surgery comprising:
a supply means for the supply of at least one fluid; and
forceps which comprises forceps-shaped electrodes with jaw parts for high-frequency surgery,
wherein the supply means is formed to dissect tissue by means of a fluid jet and is formed at or in one of the jaw parts,
wherein the forceps-shaped electrodes comprises a rigid jaw part and a movable jaw part and the supply means is formed at or within the rigid jaw part, and
wherein at least one outlet of the supply means is arranged at an inside surface of the rigid jaw part opposite the movable jaw part such that at least one fluid jet can be discharged in the direction of the movable jaw part and the at least one outlet of the supply means is displaceable relative to a longitudinal axis of the rigid jaw part such that the at least one fluid jet is displaceable relative to tissue fixed by the jaw parts.

3. The multifunction device for endoscopic surgery according to claim 1, wherein the high-frequency electrode further comprises a circular disc at the distal end of the supply means.

4. The multifunction device for endoscopic surgery according to claim 2, wherein the at least one outlet of the supply means is located in a recess of the rigid jaw part arranged parallel to a longitudinal axis of the multifunction device for surgery.

5. The multifunction device for endoscopic surgery according to claim 2, wherein the forceps is a biopsy forceps.

6. The multifunction device for endoscopic surgery according to claim 2, wherein the jaw parts are prestressed by a spring element, wherein the spring element holds the jaw parts open.

7. The multifunction device for endoscopic surgery according to claim 1, wherein the high-frequency electrode is suitable for the dissection and/or coagulation of tissue.

8. The multifunction device for endoscopic surgery according to claim 1, wherein the high-frequency electrode further comprises a hemispherical attachment at the distal end of the supply means.

9. The multifunction device for endoscopic surgery according to claim 2, wherein the movable jaw part comprises a recess arranged parallel to the longitudinal axis of the multifunction device for surgery, wherein the recess is positioned opposite the at least one outlet of the supply means.

10. A multifunction device for endoscopic surgery comprising:
a supply means for the supply of at least one fluid; and
a clamp which comprises forceps-shaped electrodes with jaw parts for high-frequency surgery,
wherein the supply means is formed to dissect tissue by means of a fluid jet and is formed at or in one of the jaw parts,
wherein the forceps-shaped electrodes comprises a rigid jaw part and a movable jaw part and the supply means is formed at or within the rigid jaw part, wherein an end piece of the supply means is a high-frequency electrode and protrudes out of a distal end of the rigid jaw part, and wherein the end piece of the supply means is movable relative to a longitudinal axis of the rigid jaw part such that a length of the electrode can be adapted according to a use thereof.

11. The multifunction device for endoscopic surgery according to claim 1, wherein the forceps is a biopsy forceps.

12. The multifunction device for endoscopic surgery according to claim 1, wherein the jaw parts are prestressed by a spring element, wherein the spring element holds the jaw parts open.

* * * * *